(12) United States Patent
Aggarwal et al.

(10) Patent No.: US 6,998,383 B2
(45) Date of Patent: Feb. 14, 2006

(54) INHIBITORS OF RECEPTOR ACTIVATOR OF NF-κB AND USES THEREOF

(75) Inventors: Bharat Aggarwal, Houston, TX (US); Bryant G. Darnay, Houston, TX (US); Sujay Singh, San Diego, CA (US)

(73) Assignee: Research Development Corporation, Carson City, NV (US)

(*) Notice: Subject to any disclaimer, the term of this patent is extended or adjusted under 35 U.S.C. 154(b) by 44 days.

(21) Appl. No.: 10/143,293

(22) Filed: May 10, 2002

(65) Prior Publication Data

US 2003/0013170 A1 Jan. 16, 2003

Related U.S. Application Data

(60) Provisional application No. 60/290,429, filed on May 11, 2001, now abandoned.

(51) Int. Cl.
*A61K 38/18* (2006.01)
*C07K 14/475* (2006.01)
*C07K 19/00* (2006.01)
*C12N 5/02* (2006.01)

(52) U.S. Cl. .............. 514/2; 435/375; 514/12; 530/300; 530/324; 530/350

(58) Field of Classification Search .......... 530/300, 530/350, 324; 435/375; 514/2, 12
See application file for complete search history.

(56) References Cited

U.S. PATENT DOCUMENTS 5,843,678 A 12/1998 Boyle .................. 435/7.1
6,017,729 A 1/2000 Anderson et al. .......... 435/69.1
6,271,349 B1 8/2001 Dougall et al. ............. 530/351

FOREIGN PATENT DOCUMENTS

GB WO 99/58674 11/1999

OTHER PUBLICATIONS

Caldwell, Yakubutsu Dotai (Xenobiotic Metabolism and Disposition), 1996, vol. 11(1): pp. 119–125.*
Yasuda, H. et al.: Identity of Osteoclastogenesis Inhibitory Factor (OCIF) and Osteoprotegerin (OPG); A Mechanism by which OPG/OCIF Inhibits Osteoclastogenesis in Vitro, *The Endocrine Society*, 1998, vol. 139, No. 3.
Zhang, Y. Et al.: Tumor Necrosis Factor–a (TNF) Stimulates RANKL–induced Osteoclastogenesis via Coupling of TNF Type 1 Receptor and RANK Signaling Pathways, *The Journal of Biological Chemistry*, 2001, vol. 276, No. 1, pp. 563–568.
Takayanagi, H. et al.: T–cell–mediated regulation of Osteoclastogenesis by signalling cross–talk between RANKL and IFN–γ, *Nature*, 2000, vol. 408.

* cited by examiner

*Primary Examiner*—Terry McKelvey
(74) *Attorney, Agent, or Firm*—Fulbright & Jaworski L.L.P.

(57) ABSTRACT

The present invention provides a RANK (receptor activator of NF-κB) inhibitor consisted of a TRAF-6 (TNF receptor-associated factor-6) binding domain attached to a leader sequence. The peptide inhibitor inhibits RANKL (RANK ligand)-mediated osteoclast differentiation, thus indicating that targeted disruption of interaction between RANK and TRAF6 may prove useful as a therapeutic for metabolic bone disorders, leukemia, arthritis, and metastatic cancer of the bone.

13 Claims, 9 Drawing Sheets

| | | | |
|---|---|---|---|
| hCD40 | 230 | KQEPQEINF | (SEQ ID NO.1) |
| mCD40 | 230 | RQDPQEMED | (SEQ ID NO.2) |
| hRANK | 341 | RQMPTEDEY | (SEQ ID NO.3) |
| hRANK | 374 | FSEPLEVGE | (SEQ ID NO.4) |
| hRANK | 450 | RNPPGEDCE | (SEQ ID NO.5) |
| mRANK | 337 | RKIPTEDEY | (SEQ ID NO.6) |
| mRANK | 370 | FQEPLEVGE | (SEQ ID NO.7) |
| mRANK | 444 | GNTPGEDHE | (SEQ ID NO.8) |
| hIRAK1 | 539 | PPSPQENSY | (SEQ ID NO.9) |
| hIRAK1 | 582 | PNQPVESDE | (SEQ ID NO.10) |
| hIRAK1 | 701 | RQGPEESDE | (SEQ ID NO.11) |
| mIRAK | 503 | SPSPQENSY | (SEQ ID NO.12) |
| mIRAK | 546 | PNQPVESDE | (SEQ ID NO.13) |
| mIRAK | 666 | SQGPEESDE | (SEQ ID NO.14) |
| hIRAK2 | 523 | SNTPEETDD | (SEQ ID NO.15) |
| hIRAK2 | 554 | PLLPTENGE | (SEQ ID NO.16) |
| hIRAK-M | 475 | PSIPVEDDE | (SEQ ID NO.17) |
| hRIP2 | 191 | IYMPPENYE | (SEQ ID NO.18) |
| Consensus | | PxExx(Ar/Ac) | |

Fig. 1A

```
L-T6Bp-1    AAVALLPAVLLALLAPRKIPTEDEYTDRPSQPST
                                                    (SEQ ID NO.19)
L-T6Bp-2    AAVALLPAVLLALLAPIPPFQEPLEVGEND
                                                    (SEQ ID NO.20)
  T6Bp-1    CRKIPTEDEYTDRPSQPST                     (SEQ ID NO.21)
  T6Bp-2    CIPPFQEPLEVGEND                         (SEQ ID NO.22)
```

Fig. 1B

INHIBITORS OF RECEPTOR ACTIVATOR OF NF-κB AND USES THEREOF

CROSS-REFERENCE TO RELATED APPLICATION

This non-provisional patent application claims benefit of provisional patent application U.S. Ser. No. 60/290,429, filed May 11, 2001, now abandoned.

BACKGROUND OF THE INVENTION

1. Field of the Invention

The present invention relates generally to the fields of cytokine biology and bone diseases. More specifically, the present invention provides inhibitors of receptor activator of NF-κB (RANK) for therapy of disorders such as diseases associated with bone resorption.

2. Description of the Related Art

Members of the TNF and TNF receptor superfamilies play critical roles in the initiation and regulation of the immune response (1–3). Although members of these families share many overlapping biological functions, it appears from gene knockout studies that they have unique features. One such receptor/ligand pair, receptor activator of NF-κB (RANK) and its ligand (RANKL/TRANCE/ODF/OPGL), is critically involved in regulation of bone remodeling and osteoclastogenesis (4). From knockout gene studies in mice, RANKL also functions in lymph node organogenesis and lymphocyte development (5). Furthermore, receptor activator of NF-κB and RANKL are implicated in the interactions between T cells and dendritic cells during the immune response (6).

As indicated by its name, receptor activator of NF-κB stimulates activation of nuclear factor-κB (NF-κB) (7–12), a transcription factor that regulates the expression of a large number of genes that play essential roles in immune and inflammatory responses (13). Evidence over the past several years has indicated that some of the TNF receptor family members interact with a family of adapter proteins known as TRAFs, (TNF receptor-associated factors), which participate in activation of the transcription factor NF-κB and c-Jun N-terminal kinase (JNK) (14).

The TNF receptor-associated factor family consists of six distinct proteins, each of which possesses a C-terminal homologous domain that is critical for self-association and is required for interaction with the receptors. All of the TNF receptor-associated factors, except for TRAF1 and TRAF4, also contain ring and zinc finger motifs in their N-termini, which appear to be utilized for interacting with other signaling molecules. Similar to the trimeric structure of the ligands and receptors of the TNF family, the C-terminus of the TRAF2 adapts a trimeric structure, as reported for TRAF2 in its interaction with peptides derived from TNF receptor 1 and CD40 (15, 16). This trimeric structure of the TNF receptor-associated factor molecules likely enables them to associate with downstream adapter proteins.

It has been demonstrated that TRAF2, TRAF5, and TRAF6 interact with receptor activator of NF-κB (RANK) and that receptor activator of NF-κB could activate both the NF-κB and JNK pathways (7). Subsequently, a more detailed analysis of the interaction of these TNF receptor-associated factors with receptor activator of NF-κB was reported (8). A novel TRAF6-binding motif has been identified in RANK that is distinct from the TRAF2- and TRAF5-binding domains. A homologous TRAF6-binding motif in CD40 was described using a combinatorial peptide library approach (17). The TRAF6 binding domain in RANK was sufficient for activation of NF-κB, suggesting that TRAF2 and TRAF5 are not necessary for NF-κB activation. However, it appears that the TRAF2-binding motif is sufficient for JNK activation, although the TRAF6-binding domain could also activate JNK, albeit to a lesser extent. Additionally, NIK (NF-κB inducing kinase) was also found to be required for the activation of NF-κB by receptor activator of NF-κB. In addition to TRAF2, TRAF5, and TRAF6, it has been demonstrated that TRAF1 and TRAF3 also associate with the carboxy terminus of receptor activator of NF-κB (9–12).

The role played by each TRAF molecule in RANK signal transduction remains elusive. Dominant negative mutants of TRAF2, TRAF5, and TRAF6 have been used to evaluate their role in NF-κB activation by RANK. It appears that all of the dominant negative TRAFs differentially inhibit the activation of NF-κB induced b y overexpression of RANK in 293 cells (9, 12). However, inclusion of all dominant negative mutants of TRAF2, TRAF5, and TRAF6 did not completely eliminate the activation of NF-κB induced by RANK in 293 cells (12). Stimulation of RANK also caused the recruitment of TRAF6, which in turn recruits and activates c-Src, which appears to be responsible for activation of phosphoinositol-3-kinase and protein kinase B/AKT, a molecule potentially involved in cell survival (18).

Knockout mouse models of RANKL, RANK, and osteoprotegerin have demonstrated an essential role of these molecules in osteoclastogenesis. The biological importance of these molecules is underscored by the induction of severe osteoporosis by targeted disruption of osteoprotegerin and by the induction of osteopetrosis by targeted disruption of RANKL or by overexpression of osteoprotegerin (5, 19, 20). Thus, osteoclast formation may be attributed to the relative ratio of RANKL to osteoprotegerin in the microenvironment of bone marrow, and alterations in this balance may be a major cause of bone loss in many metabolic bone disorders.

Similar to RANKL−/− mice, targeted disruption of receptor activator of NF-κB also lead to an osteopetrotic phenotype (21, 22). Both RANK−/− and RANKL−/− mice exhibited absence of osteoclasts, indicating the essential requirement of these molecules for osteoclastogenesis. Additionally, mice lacking TRAF6 (23–25), c-Src (26), c-Fos (27), or the NF-κB subunits p50/p52 (28, 29) also display an osteopetrotic phenotype. Although these mutant mice have osteoclasts, these cells apparently have defects in bone resorption. Thus, RANKL and receptor activator of NF-κB as well as their cytoplasmic signaling molecules are required for osteoclastogenesis.

Of the TRAF molecules that bind to receptor activator of NF-κB, only TRAF6 appears to be essential for osteoclast differentiation as indicated in mice lacking TRAF6. Thus, t h e interaction of receptor activator of NF-κB with TRAF6 may be a unique target for therapeutic intervention, and the ability to disrupt this interaction by a competitive, cell permeable peptide remains to be investigated.

Thus, the prior art is deficient in methods of disrupting the interaction between receptor activator of NF-κB and TRAF6 in order to inhibit RANKL signaling and osteoclast differentiation induced by RANKL. Such inhibitors would be useful as therapeutics in bone disorders and cancer associated with increased bone resorption. The present invention fulfills this long-standing need and desire in the art.

SUMMARY OF THE INVENTION

TRAF6 (TNF receptor-associated factor 6) is a critical adapter protein for Receptor Activator of NF-κB (RANK)

signaling. The present invention discloses a novel TRAF6 decoy peptide (T6DP) with and without a peptide leader sequence that allows for transversing the cellular membrane. Evidence disclosed herein indicate that the TRAF6 decoy peptide inhibits early events associated with RANKL signaling and RANKL-mediated osteoclast differentiation only when the leader sequence is attached. This data indicates that targeted disruption of interaction between Receptor Activator of NF-κB and TRAF6 may prove useful as a therapeutic for metabolic bone disorders, leukemia, arthritis, and metastatic cancer of the bone.

The present invention provides polypeptides that inhibit signaling mediated by TNF receptor-associated factor 6 (TRAF6), wherein the polypeptides comprise of a TRAF6 binding domain and a leader signal sequence. The present invention is further drawn to methods of inhibiting Receptor Activator of NF-κB Ligand (RANKL)-induced osteoclast differentiation using the polypeptides disclosed herein.

In another aspect of the present invention, there is provided a non-peptide analog that mimics the function of the polypeptide disclosed herein, wherein said non-peptide analog inhibits signaling mediated by TRAF6. The present invention is further drawn to methods of inhibiting Receptor Activator of NF-κB Ligand (RANKL)-induced osteoclast differentiation using a non-peptide analog that mimics the function of the polypeptide disclosed herein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A and 1B show the novel TRAF6 binding domain in RANK.

FIG. 1A shows (he consensus sequence of the TRAF6 binding domain. The region within the amino acid sequence of CD40 (residues 230–245) that specifically interacts with TRAF6 (38) was used as the template for alignment of RANK, IRAK1, and IRAK2. Identical residues are in bold. A consensus motif is shown on the bottom.

FIG. 1B shows the peptides used in the present study. The hydrophobic domain of Kaposi fibroblast growth factor signal sequence (underlined) (36) was attached to the two potential TRAF6 binding domains from murine receptor activator of NF-κB. Additionally, two peptides lacking the leader sequence were synthesized.

FIG. 2A shows RANKL-induces TRAP positive osteoclasts. RAW264.7 cells were plated in 12-well plates and stimulated with RANKL (30 ng/ml) for 4 days. Cells were stained for TRAP essentially as described below. Photographs were taken using a 10× objective lens.

FIG. 2B shows L-T6DP-1 inhibits osteoclast differentiation. RAW cells were plated as described in FIG. 2A and treated with RANKL in the presence of 1, 30, or 100 μM of peptides as indicated. On day 4 cells were stained and evaluated as in FIG. 2A.

FIG. 2C shows L-T6DP-1 inhibits the total number of TRAP positive osteoclasts induced by RANKL. RAW264.7 cells were plated in 48-well plates in triplicate and treated with RANKL in the presence of increasing amounts of the indicated peptides. After 4–5 days, the cells were stained for TRAP and the total numbers of osteoclasts were counted as described below.

FIG. 3A shows mouse-derived monocytes were plated in 48-well plates in triplicate and costimulated with murine M-CSF (10 ng/ml) and RANKL (30 ng/ml) in the absence (0) or presence of the indicated peptides. After 6–7 days, the cells were fixed and stained for TRAP. The numbers of multi-nucleated, TRAP positive osteoclasts were counted.

FIG. 3B shows LT6DP-1 inhibits osteoclast differentiation of mouse-derived monocytes. Mouse-derived monocytes were plated in 48-well plates and costimulated as in FIG. 3A with murine M-CSF (10 ng/ml) and RANKL (30 ng/ml) in the absence (left panel) or presence of the indicated peptides. After 6–7 days, the cells were fixed and stained for TRAP. A representative field from each well was taken at a magnification of 10×.

FIG. 4A shows inhibition of RANKL-mediated NF-κB activation by L-T6Bp-1. RAW264.7 cells were plated in 6-well plates and treated with the indicated peptides for 5 h, then treated with RANKL (10 nM) for 15 mm. Nuclear and cytoplasmic extracts were prepared and a gel mobility shift assays was performed with 8 μg of nuclear extracts as described below.

FIG. 4B shows inhibition of IκB degradation by L-T6DP-1. Cytoplasmic extracts (30 μg) from FIG. 4A were immunoblotted with anti-IκB as described below.

FIG. 4C shows L-T6DP-1 inhibits TRAF6 from binding to the receptor activator of NF-κB cytoplasmic domain. Cellular extracts from human 293 cells transfected with either FLAG-TRAF2, -TRAF5, or -TRAF6 were mixed with GST or GST-RANKed in the absence or presence of 100 μM of the indicated peptides. A GST-pull down assay was performed as described below. The bound TRAFs were visualized by immunoblotting with anti-FLAG antibodies.

FIG. 5A shows inhibition of RANKL-mediated JNK activation by L-T6DP-1. RAW264.7 cells were plated in 6-well plates and treated with the indicated peptides for 6 h, then treated with RANKL (10 nM) for 15 mm. Whole cell extracts were prepared and 30 μg of cell lysate was immunoprecipitated with anti-JNK1. In vitro kinase assays were performed using GST-Jun (1–79) as the substrate as described below.

FIG. 5B and FIG. 5C show inhibition of RANKL-mediated ERK and p38 activation by L-T6DP-1. Whole cell extracts (30 μg) from FIG. 5A were separated by 10% SDS-PAGE and electroblotted onto a nitrocellulose membrane. The membranes were first immunoblotted with the indicated phospho-specific antibody and then stripped and re-probed with the indicated antibodies as described below.

FIG. 6A: Breast cancer cells (500/well) were plated in 24-well plates in the absence or presence of RAW cells (10000/well) and in the absence or presence of L-T6DP-1 or T6DP-1 (100 μM). After 5 days. the cells were fixed, stained for TRAP, and photographed with a 10× objective lens.

FIG. 6B shows RAW cells were cultured alone or in the presence of the indicated cells on synthetic bone slides (BD BiCoat Osteologic MultiTest Slides). After 6 days, the cells were removed by washing the slide in bleach for 5 minutes and then washing thoroughly with distilled water. The slide was air dried and then photographs were taken with a light microscope (10× objective lens). The ghosts of osteoclasts (arrow) can be seen where functional osteoclasts destroyed the synthetic bone matrix.

FIG. 6C shows normal breast epithelial cells (MCF10A, 1000/well) grown in the presence of RAW and stained for TRAP as indicted in FIG. 6A. The right panel includes the addition of RANKL (100 ng/ml) to the co-culture.

DETAILED DESCRIPTION OF THE INVENTION

Figure 2A:
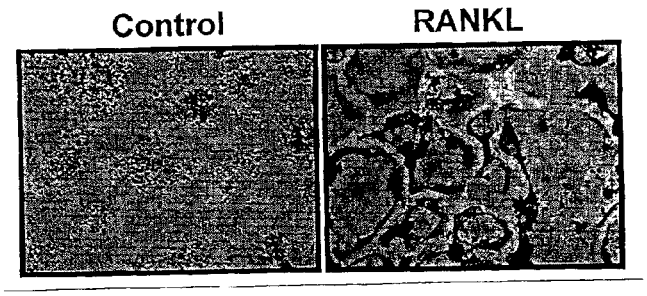
FIGS. 2A–2C show L-T6Bp-1 inhibits RANKL-mediated osteoclast differentiation in RAW264.7 cells.

Receptor activator of NF-κB (RANK), a recently described member of the TNF receptor superfamily, is expressed primarily by dendritic cells, osteoclast progenitors, activated B and T cells and osteoclasts. By binding to its ligand (RANKL), the receptor activator of NF-κB causes the sequential recruitment of adapter molecules responsible for activation of signaling processes. These pathways lead to activation of protein kinases, which in turn activate transcription factors leading to changes in gene expression that alter the function of the cell.

Knockout mouse models of RANKL, RANK, and osteoprotegerin (OPG), a secreted soluble receptor that binds RANKL, have demonstrated an essential role of these molecules in osteoclastogenesis (i.e., bone remodeling). The biological importance of these molecules is underscored by the induction of severe osteoporosis by targeted disruption of osteoprotegerin and by the induction of osteoperosis by targeted disruption of RANKL, the receptor activator of NF-κB, or by transgenic expression of osteoprotegerin. These results indicate that osteoclast formation may be attributed to the relative ratio of the receptor activator of NF-κB ligand to osteoprotegerin in the microenvironment of bone marrow, and alterations in this balance may be a major cause of bone loss in many metabolic bone disorders. Hence, RANK/RANKL/osteoprotegerin have a major role in bone diseases and cancer-induced bone destruction that are due to increased osteoclastic activity.

In addition to osteoporosis, recent reports suggest a potential role of these molecules in other diseases including rheumatoid arthritis, giant cell tumor of bone, Paget's disease, and familial expansile osteolysis (due to a mutation in exon 1 of the receptor activator of NF-κB ). A T cell lymphoproliferative disorder has also been identified in which dysregulation of the receptor activator of NF-κB and RANKL contributes to the survival of malignant T cell clone.

It has been recognized that breast and prostate cancers have the ability to invade and grow as metastases in bone causing osteolytic lesions. In metastatic tumor mouse models in which the tumor causes increased osteoclastogenesis and bone destruction, systemic administration of osteoprotegerin reduces tumor-mediated bone destruction and pain associated with bone cancer. Thus, development of drugs that target inhibition of the receptor activator of NF-κB signaling are potential therapeutics for metabolic bone disorders and cancer.

The cytoplasmic domain of receptor activator of NF-κB interacts with TRAF family members, specifically TRAF1, 2, 3, 5, and 6. Stimulation of the receptor activator of NF-κB activates members of the MAPK family (i.e., JNK, p38, ERK) and IKKs, which lead to activation of transcription factors AP1 and NF-κB. The interactions of TRAF2, TRAF5, and TRAF6 with receptor activator of NF-κB have been reported and it was demonstrated that receptor activator of NF-κB could activate both the NF-κB and JNK pathways. Subsequently, a novel TRAF6 binding motif was identified in receptor activator of NF-κB that is distinct from the TRAF2 and TRAF5 binding domains.

The TRAF6 binding domain in the receptor activator of NF-κB was sufficient for activation of NF-κB, suggesting that TRAF2 and TRAF5 are not necessary for NF-κB activation. In support of these findings, TRAF6-deficient mice develop osteopetrosis due to a defect in osteoclastogenesis, which is not found in either the TRAF2- or TRAF5-deficient mice.

Since TRAF6 appears to be the critical adapter protein for the receptor activator of NF-κB signaling, the present invention develops a novel TRAF6 decoy peptide (T6DP) with and without a peptide leader sequence that allows for transversing cellular membrane. Evidence disclosed herein indicate that the TRAF6-decoy peptide inhibits RANKL signaling transduction and RANKL-mediated osteoclast differentiation, but only when the leader sequence is attached. These data indicate that targeted disruption of the interaction between receptor activator of NF-κB and TRAF6 would be useful as a therapeutic for metabolic bone disorders, leukemia, multiple myeloma, arthritis, and metastatic cancer of the bone.

The present invention is drawn to polypeptides that inhibit signaling mediated by TNF receptor-associated factor 6 (TRAF6). These polypeptides comprise a TRAF6 binding domain and a leader signal sequence. A number of approaches may be utilized by a person having ordinary skill in this art to search for TRAF6 inhibitory polypeptides; two approaches are, for example, screening peptide libraries or synthesizing overlapping peptides from the cytoplasmic domains of RANK or TRAF6. In one embodiment of the present invention, the polypeptide comprises of sequence selected from the group consisting of SEQ ID No. 19 and 20. Since TRAF6 also mediates signaling induced by a number of molecules such as IL-1, LPS, IL-18, and CD40L, the polypeptides claimed herein may inhibit RANKL mediated signaling as well as signaling induced by these other molecules.

The polypeptides disclosed herein may contain a TRAF6 binding domain derived from CD40, Receptor Activator of NF-κB, IL-1 receptor-associated kinase 1 (IRAK1), IL-1 receptor-associated kinase 2 (IRAK2), IRAK-M or RIP2. Preferably, the TRAF6 binding domain comprises of sequence selected from the group consisting of SEQ ID No. 1–18.

The leader signal sequence attached to the TRAF6 binding domain in the polypeptides disclosed herein may be derived from a number of different proteins. Representative leader signal peptides include Kaposi fibroblast growth factor signal sequence, HIV-1 Tat (48–60), D-amino acid-substituted HIV-1 Tat (48–60), arginine-substituted HIV-1 Tat (48–60), *Drosophila* Antennapaedia (43–58), viral RNA binding peptide that comprises 7 or more arginines, DNA binding peptide that comprises 7 or more arginines and polyarginine polypeptide that has 6 to 8 arginines. These arginine-rich signal sequences that can be used for delivery of exogenous proteins into cells are well known in the art (39). For example, Futaki et al. (39) has reported various arginine-rich peptides that have translocation activities very similar to that of HIV-1 Tat (48–60). These arginine-rich peptides include HIV-1 Rev (34–50), HTLV-II Rev (4–16), brome mosaic virus Gag (7–25), flock house virus coat protein (35–49), human c-Fos (139–164), human c-Jun (252–279) and yeast transcription factor GCN4 (231–252).

The present invention is also drawn to a method of inhibiting Receptor Activator of NF-κB Ligand (RANKL)-induced osteoclast differentiation using the polypeptides disclosed herein, wherein inhibition of interaction between the receptor activator of NF-κB and TRAF6 by these polypeptides result in inhibition of RANKL-induced osteoclast differentiation. This method can be used to inhibit osteoclast differentiation induced by breast cancer cells. The polypeptide can be applied to the cells by a number of methods well known in the art such as liposomes, viruses or other gene delivery vectors. For example, the ProVectin™ protein delivery reagent is a unique lipid-based formulation that allows delivery of the polypeptides disclosed herein or other bioactive molecules into a broad range of cell types.

In another aspect of the present invention, there is also provided a method of inhibiting osteoclast differentiation in a n individual by the polypeptide inhibitors disclosed herein. In general, the individual would have a disease comprising a metabolic bone disorder, leukemia, arthritis, multiple myeloma, or metastatic cancer of the bone.

The present invention also provides a pharmaceutical composition comprising a pharmaceutically acceptable carrier and the polypeptide inhibitors disclosed herein. The phrase "pharmaceutically acceptable" refers to molecular entities and compositions that do not produce an allergic or similar untoward reaction when administered to a subject. The preparation of an aqueous composition that contains a protein as an active ingredient is well understood in the art.

A person having ordinary skill in this art would readily b e able to determine, without undue experimentation, the appropriate dosages and routes of administration of the active component of the present invention. When used in vivo for therapy, the active composition(s) of the present invention is administered to the patient or an animal in therapeutically effective amounts, i.e., amounts that inhibit RANKL-mediated osteoclast differentiation. See Remington's Pharmaceutical Science, 17th Ed. (1990) Mark Publishing Co., Easton, Penn.; and *Goodman and Gilman's: The Pharmacological Basis of Therapeutics* 8th Ed (1990) Pergamon Press.

The present invention is further drawn to non-peptide analogs that mimic the functions of the polypeptide disclosed herein, wherein these non-peptide analogs inhibit signaling mediated by TRAF6. Low molecular weight, non-peptide molecules that mimic the inhibitory polypeptides disclosed herein can serve as robust tools to help establish the role of TRAF6-mediated signaling in models of physiological and pathophysiological processes as well as serving as therapeutic agents in their own right. A number of reports have disclosed the rationale and strategy for the design of low molecular weight, non-peptide molecules that are amenable to high resolution analysis and rapid modification (40–42). The present invention is also drawn to a method of inhibiting Receptor Activator of NF-κB Ligand (RANKL)-induced osteoclast differentiation using these non-peptide analogs, wherein inhibition of interaction between the receptor activator of NF-κB and TRAF6 by said non-peptide analogs result in inhibition of RANKL-induced osteoclast differentiation. This method can be used to inhibit osteoclast differentiation induced by breast cancer cells.

The following examples are given for the purpose of illustrating various embodiments of the invention and are not meant to limit the present invention in any fashion.

EXAMPLE 1
Reagents, Cell Lines, and Antibodies

The human embryonic kidney 293 cell line and the mouse macrophage cell line RAW264.7 were obtained from the American Type Culture Collection (Rockville, Md.). The 293 cells were cultured in MEM supplemented with 10% fetal bovine serum and antibiotics. RAW264.7 cells were cultured in DMEM-F12 supplemented with 10% fetal bovine serum and antibiotics. Monoclonal antibodies to phospho-ERK, p38, and JNK were purchased from New England Biolabs. Goat anti-rabbit IgG-conjugated horseradish peroxidase was purchased from BioRad Laboratories (Hercules, Calif.). Anti-JNK1 and anti-IκB were purchased from Santa Cruz Biotechnology (Santa Cruz, Calif.). Goat anti-mouse IgG-conjugated horseradish peroxidase was purchased from Transduction Laboratories (Lexington, Ky.). Protein A/G Sepharose beads was purchased from Pierce (Rockford, Ill.), and anti-FLAG was purchased from Sigma (St. Louis, Mo.). Staining for tartrate resistance acid phosphatase (TRAP) positive osteoclasts was performed essentially as described (30) or by using an acid phosphatase kit from Sigma.

EXAMPLE 2
Expression Plasmids

Expression plasmids encoding mouse FLAG-tagged TRAF5 and TRAF6 (31) were provided by H. Nakano (Juntendo University, Tokyo, Japan) and FLAG-tagged TRAF2 was provided by J. Ni (Human Genome Sciences, Inc.). Expression vectors and purification of GST-fusion proteins for GST, GST-receptor activator of NF-κB cytoplasmic domain, and GST-Jun (1–79) have been previously described (7, 8). The expression vector of full-length murine RANKL (also known as TNF-related activation-induced cytokine (TRANCE) (pcDNA3.1-TRANCE) was provided by Y. Choi (Rockefeller University, New York, N.Y.).

To generate a bacterial expression vector for RANKL, specific 5' and 3' primers with HindIII and NotI sites, respectively, were used to amplify the DNA which encodes residues 157–316 of RANKL from the pcDNA3-TRANCE template. The PCR product was digested with HindIII/NotI and ligated in-frame with a HA-tag (N-terminal) and a histidine tag (C-terminal) into the expression vector pHB6 (Boerhinger Mannheim). Soluble RANKL was expressed and purified using Ni-agarose.

EXAMPLE 3
Transient Transfections and Western Blotting 293 cells were plated at $0.6 \times 10^6$ cells/well on 6-well plates and transfected the next day as described (8). Total amount of plasmid DNA was kept constant by adding empty pCMVFLAG1 vector. Cells and the conditioned supernatants were harvested 24–36 h after transfection. Lysates were prepared as described (8). For western blot analysis, whole-cell lysates (15–30 $\mu$g) or proteins from GST-affinity precipitation were separated by 8.5% SDS-PAGE, electroblotted onto nitrocellulose membranes, and incubated with the indicated antibodies. The membranes were then developed using the enhanced chemiluminescence (ECL) system (Amersham, Chicago, Ill.).

EXAMPLE 4
In Vitro Osteoclast Differentiation

Primary bone marrow monocytes (BM) or RAW264.7 cells were cultured in 48-well dishes at a density of 1×10⁵ cells/well or 2×10³ cells/well, and then treated with the indicated factors at the beginning of the culture and during a medium change on day 3. Osteoclast formation was assessed by counting the total number of multi-nucleated (>3 nuclei), TRAP-positive cells present per well between day 7 and 10 (BM) or on day 5 (RAW264.7) (30).

EXAMPLE 5
GST-RANK Fusion Protein Affinity Binding Assays

Equivalent amounts of GST or GST-RANK cytoplasmic domain (GST-RANKed) fusion protein attached to 20 μl of glutathione agarose beads were mixed with lysates (50 μg) from 293 cells programmed to express the epitope-tagged TRAF protein and the indicated peptides in binding buffer (20 mM TRIS, pH 8, 150 mM NaCl, 1 mM DTT, 2 mM EDTA, and 0.1% NP-40) and allowed to rotate for 1 h at 4° C. The beads were collected by centrifugation, washed three times in binding buffer, and then washed once in low-salt buffer (20 mM TRIS, pH 8, 50 mM NaCl, and 1 mM DTT). Bound proteins were eluted with addition of SDS-sample buffer and boiled. The eluted proteins were subjected to 7.5% SDS-PAGE and western blot analysis was performed with anti-FLAG antibodies.

EXAMPLE 6
Immune Complex Kinase Assays

Lysates were prepared from RAW cells stimulated with RANKL as indicated in the legends to the figures. Approximately 30 μg was then used for immunoprecipitation with indicated antibodies and protein A/G Sepharose beads for 1 h. Beads were collected by centrifugation, washed three times in lysis buffer, and then washed two times in low-salt buffer. JNK activity was analyzed using exogenous GST-Jun (1–79) as a substrate as previously described (8). Kinase activity was quantitated using a PhosphoImager and Imagequant Software (Molecular Dynamics, Sunnyvale, Calif.).

EXAMPLE 7
Electrophoretic Mobility Shift Assays (EMSA)

Nuclear extracts were prepared from transfected cells essentially as described (34). Equivalent amounts of nuclear protein were used in an EMSA reaction with $^{32}$P-labeled NF-κB oligonucleotide from HIV-LTR as described (34). NF-κB activation was quantitated using a PhosphoImager and Imagequant Software.

EXAMPLE 8
TRAF6 Binding Domain

A novel TRAF6 binding domain in RANK, which binds to only TRAF6 but not TRAF2 or TRAF5, has been identified previously (8). When transfected in 293 cells, this region of the receptor activator of NF-κB was sufficient for activation of NF-κB (8). Structure-based sequence alignment of TRAF6-binding sites in human and mouse CD40 and RANK led to the definition of a TRAF6-binding motif PxExx(Ar/Ac) (Ar for aromatic and Ac for acidic residues) (FIG. 1A). Careful examination of the RANK sequence indicates that there are three potential TRAF6-binding sites (FIG. 1A).

TRAF6 is the only TRAF family member that participates in the signal transduction of both the TNF receptor superfamily and the interleukin-1 receptor (IL-1R)/Toll-like receptor (TLR) superfamily. The best-characterized TRAF6 signaling pathway for the IL-1R/TLR superfamily involves IRAK, an adapter kinase upstream of TRAF6. Upon receptor stimulation, IRAK becomes oligomerized and interacts with TRAF6 (43). It was found that full-length IRAK contains three potential TRAF6-binding sites (FIG. 1A). Two IRAK homologues, IRAK-2 and IRAK-M, also contain two and a single potential TRAF6-binding site, respectively (FIG. 1A). This is in keeping with the implicated role of IRAK-2 and IRAK-M in IL-1 signaling and the role of IRAK-2 in TLR4 signaling. In addition, it was found that the kinase RIP2, which can activate NF-κB and induce cell death, also contains a putative TRAF6-binding site (FIG. 1A). The presence of TRAF6-binding sites in these various molecules suggests that TRAF6 may play a role in mediating multiple signaling cascades.

Delivery of peptides or proteins across cellular membranes can be achieved by covalent attachment of the peptide to molecules that can freely pass through the membrane (35). For example, the hydrophobic domain of Kaposi fibroblast growth factor signal sequence was attached to the nuclear localization signal from the p50 subunit of NF-κB to allow for translocation across the membrane (36). In the present invention, this hydrophobic sequence was attached to peptides derived from murine RANK, namely L-T6DP-1 which contains the known TRAF6 binding domain and L-T6DP-2 which contains a similar motif (FIG. 1B). In addition, both of these peptides were synthesized without the leader sequence, resulting in peptides that were not be able to transverse cellular membrane (FIG. 1B).

EXAMPLE 9
TRAF6-decoy Peptides Inhibit RANKL-mediated Osteoclast Differentiation in RAW264.7 Cells The mouse macrophage cell line RAW264.7 express the receptor activator of NF-κB on their cell surface and when stimulated with the receptor activator of NF-κB ligand differentiate into multi-nucleated, tartrate resistant acid phosphatase (TRAP) positive osteoclasts after 4–5 days (FIG. 2A). To determine whether L-T6DP-1 could inhibit RANKL-mediated osteoclast differentiation, RAW264.7 cells were co-cultured with increasing concentrations of either L-T6DP-1. or T6DP-1 and 30 ng/ml RANKL for 4 days.

Figure 2B:
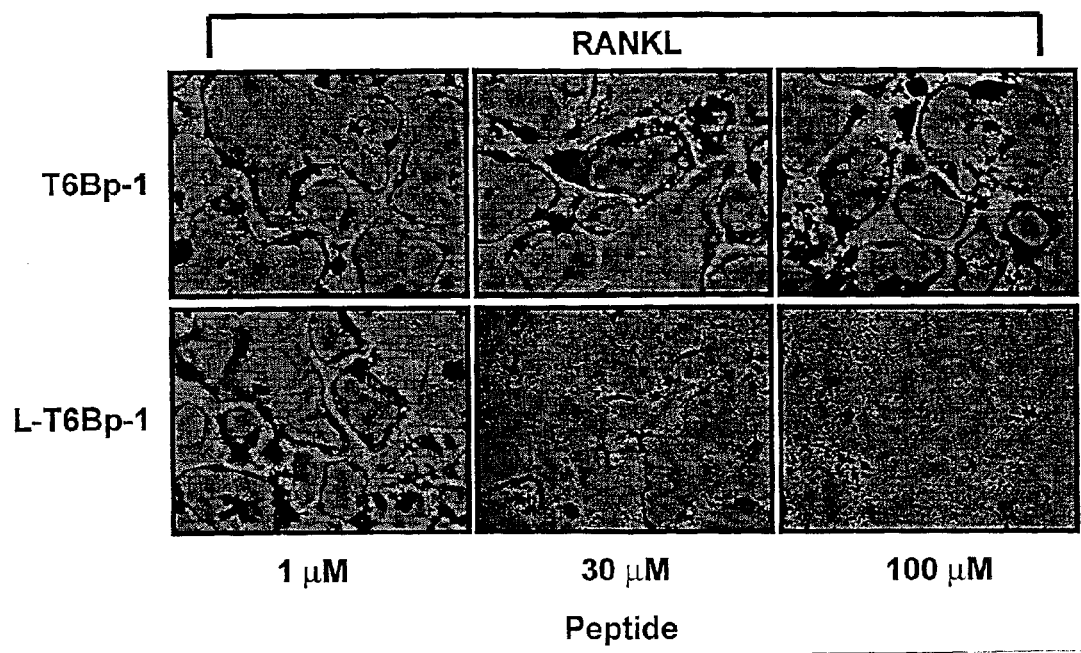
Figure 2C:
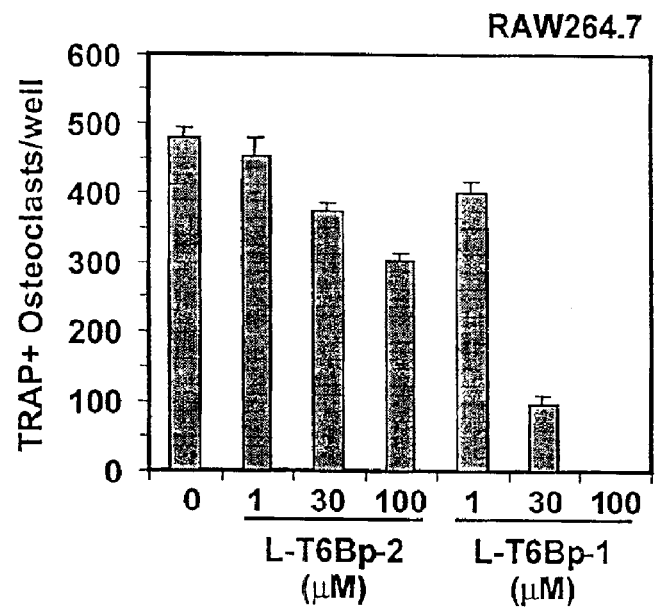

As indicated in FIG. 2B, TRAF6decoy peptide without leader sequence failed to block RANKL-mediated osteoclast differentiation; however, treatment with L-T6DP-1 caused a dose-dependent inhibition of osteoclast differentiation. Although the cells were TRAP positive after treatment with 100 μM L-T6DP-1, multi-nucleated osteoclast were not observed (FIG. 2B). Furthermore, treatment of RAW264.7 cells with RANKL in the presence of either L-T6DP-1 or L-T6DP-2 caused a dose-dependent decrease of TRAP positive osteoclasts (FIG. 2C), although L-T6DP-1 was much more efficient than L-T6DP-2.

Figure 3A:
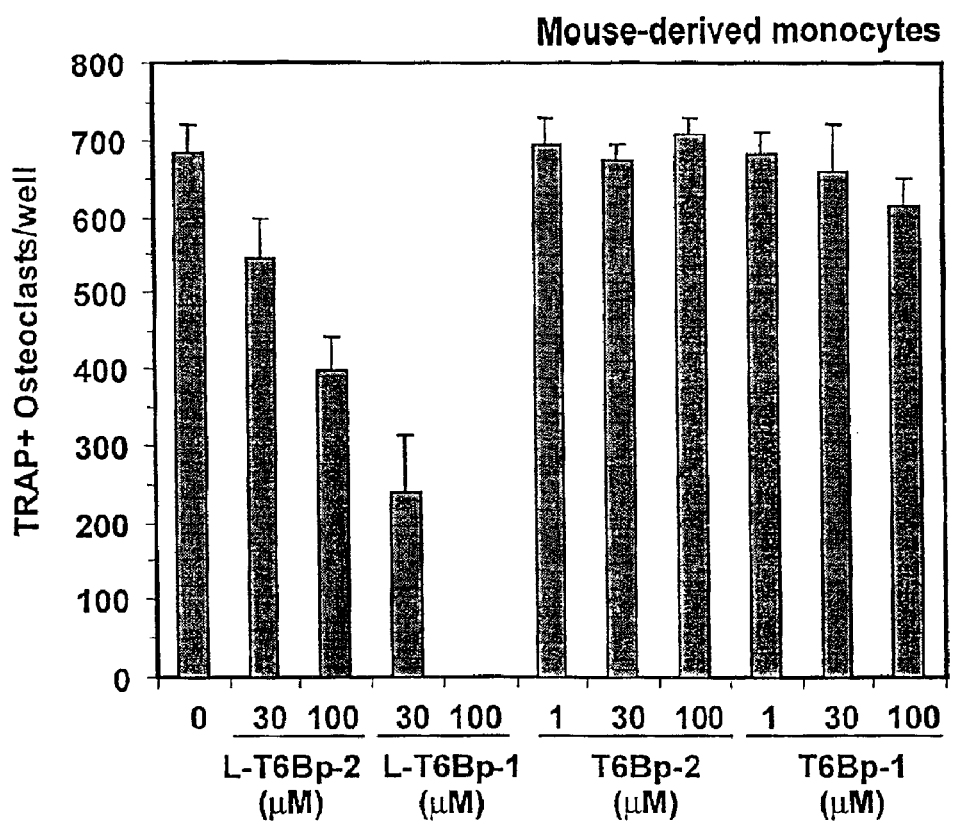
FIGS. 3A and 3B show leader TRAF6-binding peptide inhiits normal mouse derived osteoclast differentiation by RANKL and M-CSF.
Figure 3B:
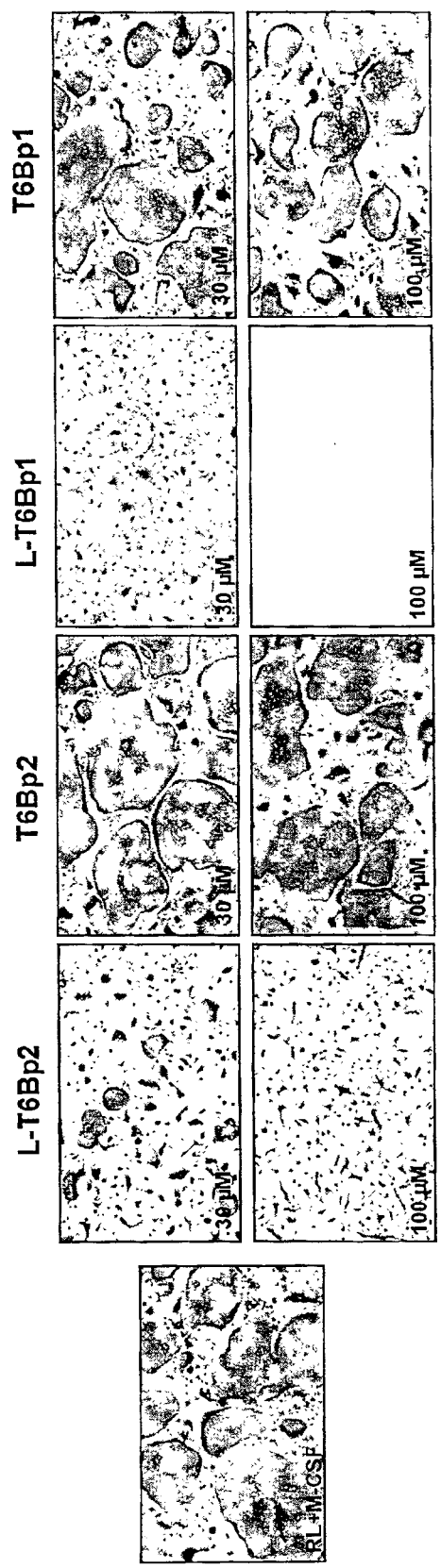

EXAMPLE 10
TRAF6decoy Peptides Inhibit RANKL-mediated Osteoclast Differentiation in Bone Marrow-derived Mouse Monocytes To further support the results obtained from the RAW264.7 cell line, the ability of these peptides to inhibit RANKL-mediated osteoclast differentiation in primary mouse-derived monocytes was tested. Costimulation of bone marrow-derived monocytes with RANKL and M-CSF cause osteoclast differentiation after 7–10 days, as determined by staining multi-nucleated, TRAP positive osteoclasts (30). Similar to the results with RAW264.7 cells, both L-T6DP-1 and L-T6DP-2 inhibited the development of TRAP positive osteoclast in a dose-dependent manner and L-T6DP-1 was much more efficient (FIGS. 3A and 3B). TRAF6 decoy peptides withouth the leader sequences failed to inhibit osteoclast differentiation (FIGS. 3A and 3B), indicating that the peptides were not toxic to the cells. Although the cells were TRAP positive after treatment with 30 μM L-T6DP-1, multi-nucleated osteoclast were not observed and at 100 μM L-T6DP-1, no osteoclasts were observed (FIG. 3B). Taken together, these results indicate that interaction of TRAF6 with RANK is essential fr RANKL-mediated osteoclast differentiation.

Figure 4A:
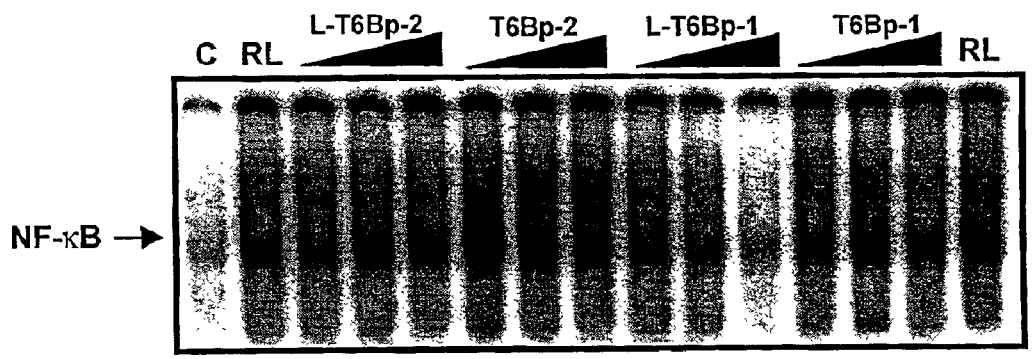
FIGS. 4A–4C show that L-T6DP-1 specifically inhibits RANKL-induced NF-κB activation and TRAF6 binding.
Figure 4B:
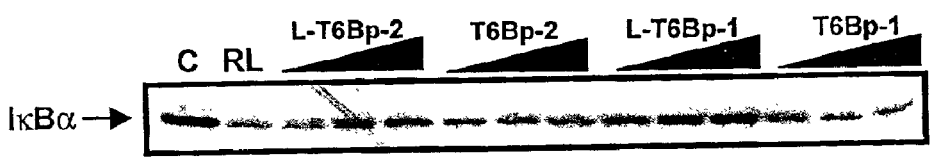

EXAMPLE 11
TRAF6Decoy Peptide Inhibits RANKL-mediated NF-κB Activation in RAW264.7 Cells A mutant form of the receptor activator of NF-κB which contains only the TRAF6 binding domain is sufficient to activate NF-κB (8), and a dominant negative TRAF6 inhibits RANK-mediated NF-κB activation in 293 cells (9). To investigate the effect of the TRAF6 binding peptides on RANKL-induced NF-κB activation, NF-κB activation was examined in RAW264.7 cells that activated NF-κB when stimulated with RANKL (37). RANKL-stimulated RAW264.7 cells activated NF-κB as indicated by a gel mobility shift assay (FIG. 4A). NF-κB activation was suppressed in a dose-dependent manner only by pre-treatment with L-T6DP-1 (FIG. 4A). The levels of IκBα coincided with the activation and repression of NF-κB as indicated in FIG. 4B. These data indicate that L-T6DP-1 specifically inhibits RANKL-mediated NF-κB activation in RAW264.7 cells.

EXAMPLE 12
TRAF6Decoy Peptide Specifically Inhibits TRAF6 Binding to the RANK Cytoplasmic Domain The cytoplasmic domain of RANK interacts with many TRAF molecules, including TRAF1, 2, 3, 5, and 6 (7–9, 11, 12). While TRAF1, 2, 3, and 5 interact with the c-terminal tail of receptor activator of NF-κB, TRAF6 interacts with a membrane proximal region of the cytoplasmic domain of the receptor activator of NF-κB. To confirm that the TRAF6-binding peptides disclosed herein were specifically inhibiting TRAF6 interaction with RANK, a competitive GST-pull down assay was performed.

Figure 4C:
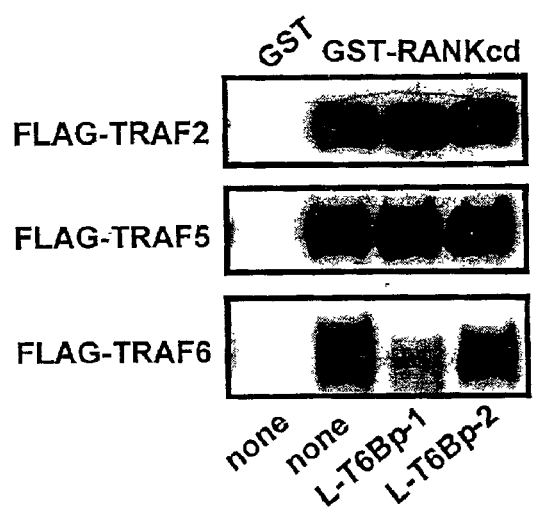

Cellular extracts containing FLAG-tagged TRAF2, TRAF5, or TRAF6 were mixed with GST-RANK cytoplasmic domain fusion protein in the presence and absence of either L-T6DP-1 or L-T6DP-2. If these peptides competed for the TRAF molecules, less FLAG-tagged protein would be observed in the western blots. As shown in FIG. 4, neither L-T6DP-1 nor L-T6DP-2 inhibited TRAF2 and TRAF5 binding to the cytoplasmic domain of RANK (FIG. 4C). Only L-T6DP-1 inhibited TRAF6 interaction with the cytoplasmic domain of RANK (FIG. 4C). These data indicate that the leader sequence did not interfere with interaction of the receptor activator of NF-κB with TRAFs and that L-T6DP-1 specifically inhibited RANK's interaction with TRAF6.

Figure 5A:
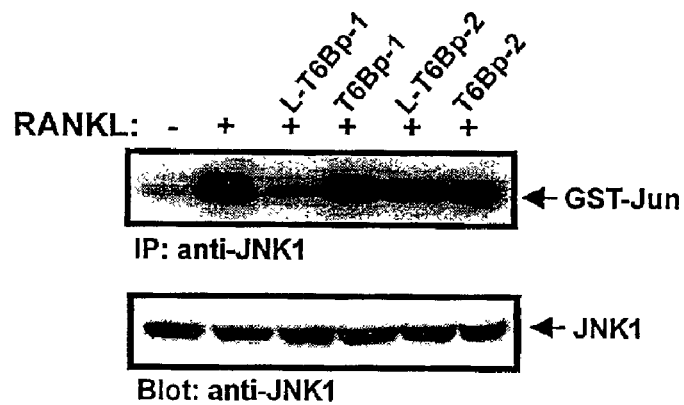
FIGS. 5A–5C show L-T6DP-1 specifically inhibits RANKL-induced JNK, ERK, and p38 kinase activation.
Figure 5B:
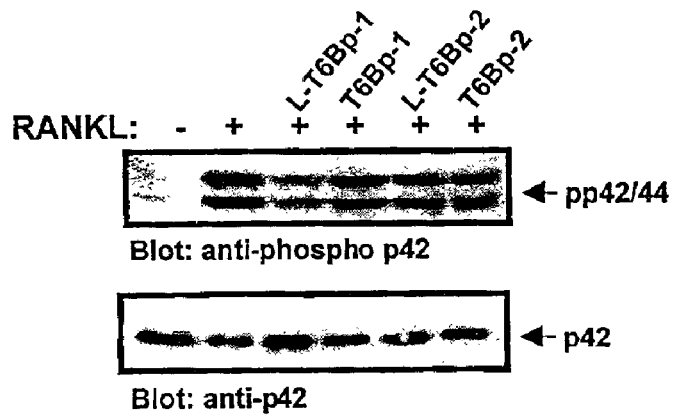
Figure 5C:
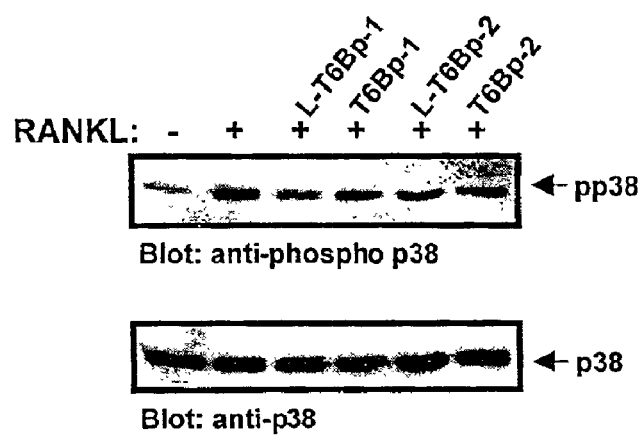

EXAMPLE 13
TRAF6Decoy Peptide Specifically Inhibits JNK, ERK, and p38 Kinase Activation by RANKL in RAW264.7 Cells Stimulation of the receptor activator of NF-κB activates members of the MAPK family including JNK, ERK and p38 kinase. The ability of the TRAF6 binding peptides to inhibit the receptor activator of NF-κB ligand-induced JNK, ERK, and p38 kinase activation was examined in RAW264.7 cells. In vitro JNK kinase assays indicated JNK is activated by RANKL and only treatment with L-T6DP-1 peptide was capable of inhibiting RANKL-mediated JNK activation (FIG. 5A). Similar to the results with JNK, only L-T6DP-1 was able to block ERK (FIG. 5B) and p38 kinase (FIG. 5C) activation induced by the receptor activator of NF-κB ligand in RAW264.7 cells. Taken with the results disclosed above, the present invention demonstrates that L-T6DP-1 is able to suppress the receptor activator of NF-κB ligand-mediated osteoclast differentiation and the receptor activator of NF-κB ligand-initiated early signaling including NF-κB, JNK, ERK, and p38 kinase activation.

EXAMPLE 14
Induction of Osteoclast Formation by Breast Cancer Cells and Inhibition by TRAF6-Decoy Peptide Breast cancer is the most common female malignancy in the U.S. and is the second leading cause of cancer death in women. Women with breast cancer are at risk for bone metastases. Five to ten percent of patients with breast cancer initially present with metastatic disease to the bone. Patients with osteolytic bone disease from metastatic breast cancer are at increased risk for pathologic fractures, bone pain, cord compression and hypercalcemia. Current standard of care for treating bone metastases is bisphosphonate therapy which delays skeletal events but does not completely prevent them. In addition, not all patients respond to this treatment. While a more effective treatment is desired, a further biological and molecular dissection of this disease is required. In fact, recently it was demonstrated that osteoprotegerin (OPG) inhibits osteolysis and decreases tumor burden in nude mouse models injected with breast cancer cells.

The ability of breast cancer cells to induce osteoclast formation and the expression of receptor activator of NF-κB/the receptor activator of NF-κB ligand/osteoprotegerin in breast cancer cells are not well defined. Few reports have demonstrated the ability of breast cancer cell lines to influence osteoclast differentiation and function; however, no evidence has been described for the direct involvement of the receptor activator of NF-κB ligand in this process. As indicated below, there is evidence to support the hypothesis that breast cancer cells directly induce osteoclast differentiation and function in the absence of osteoblast/stromal cells. Through the understanding of the biological and molecular role of the receptor activator of NF-κB ligand in breast cancer cells in the bone microenvironment and development of novel inhibitors of osteoclast formation as described herein, alternative therapeutic approaches or combination therapy may be developed to treat breast cancer patients with bone metastases.

In the present example, a co-culture assay system was developed for RAW cells and the osteoblast-like cell (osteosarcoma MG-63) which has been shown to express the receptor activator of NF-κB ligand and cause osteoclast differentiation. The number of MG-63 cells was critical for inducing RAW cells to differentiate into osteoclasts. These observations lead to a direct inverse relationship between the number of RAW cells to MG-63 cells which is required for the formation of osteoclasts. Results using RAW cells co-cultured with MG-63 (data not shown) or with breast cancer cell lines (i.e., T47D and MDA-MB-468) indicated that these breast cancer cells could in fact cause RAW cells to form TRAP+, multi-nucleated osteoclasts after 4 days (FIG. 6A) similar to RAW cells stimulated with the receptor activator of NF-κB ligand. In addition, when the breast cancer cell lines were grown in tissue culture inserts where they were separated from RAW cells by a membrane, osteoclast still formed, suggesting that direct cell-to-cell contact was not required for osteoclast differentiation (data not shown). When grown on synthetic bone slides, the osteoclasts derived from the co-culture assays were able to cause bone resorption (FIG. 6B).

Figure 6A:
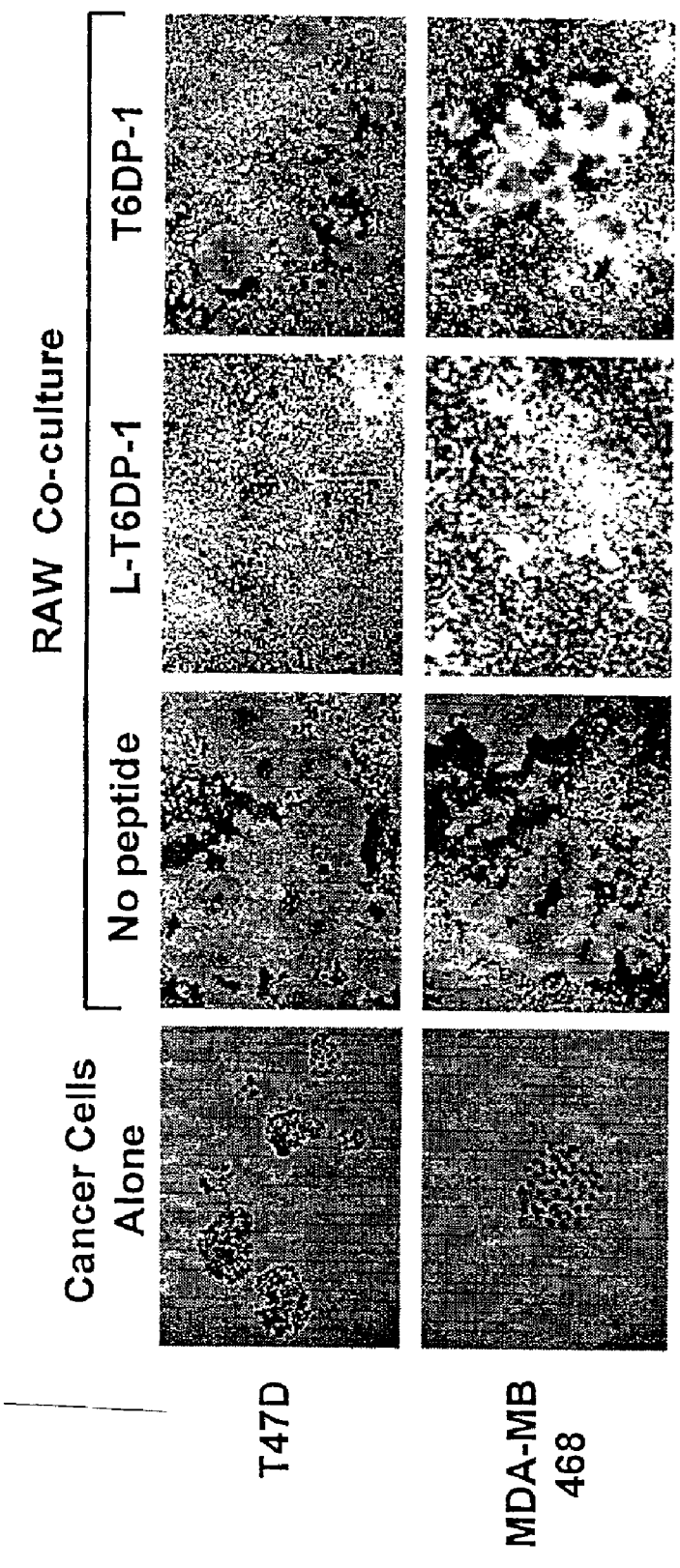
FIGS. 6A–6C show L-T6DP-1 inhibits osteoclast differentiation induced by breast cancer cells.
Figure 6B:
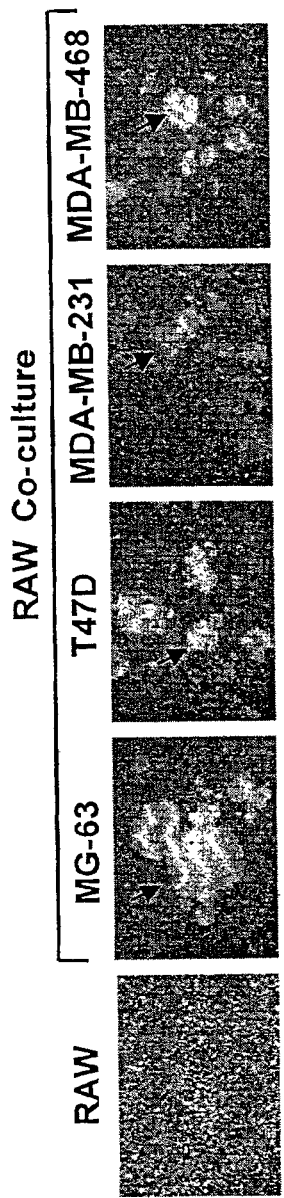
Figure 6C:
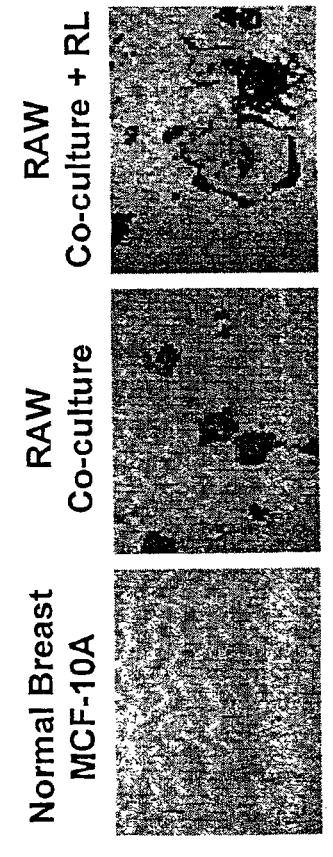

When L-T6DP-1 was added to these co-culture assays, the ability of the breast cancer cells to induce osteoclast differentiation of RAW cells was abolished, whereas T6DP-1 had no effect (FIG. 6A). Normal breast epithelial cells, MCF-10A, failed to induce osteoclast differentiation of RAW; however, osteoclasts did form if exogenous the receptor activator of NF-κB ligand was added to these co-cultures (FIG. 6C). Collectively, these data indicate that breast cancer cell lines, but not normal breast epithelial cells, can directly induce osteoclast differentiation in the absence of osteoblast/stromal cells and that L-T6DP-1 can inhibit this process.

EXAMPLE 15

Strategy to Discover Non-peptide Analogues that Inhibit RANK-TRAF6 Interaction

An ELISA-based method similar to one described previously (J. Biol. Chem., 276:12235–12240, 2001) can be used to discover small molecules that inhibit RANK-TRAF6 interaction. Briefly, peptides comprising the T6DP are biotinylated, dissolved in TRIS-buffered saline (50 mM TRIS pH 7.5, 150 mM NaCl), and added to wells in NeutrAvidin-coated 96-well microtiter plates. The plates are shaken overnight at 4° C. and then rinsed with TBS followed by TBS-BT (TBS containing 0.1% bovine serum albumin (BSA) and 0.1% Tween 20). A solution containing a test small molecule from a library is then added to the well. A solution containing 6x-histidine-tagged TRAF6 (309–522) is then added to each well. The plates are incubated for 1 h at room temperature and then washed 3 times with TBS-BT. An antibody directed against the C-terminus of TRAF6 is then added to the wells and the plates are incubated for 1 hour a t room temperature, followed by 3 washes with TBS-BT. A secondary antibody consisting of goat anti-mouse alkaline phosphatase is then added to each well and the plates are incubated for 1 hour at room temperature, followed by 3 washes with TBS-BT. The plates are then assayed for alkaline phosphatase activity using a fluorescent plate reader as previously described (Darnay et al., J. Biol. Chem. 274:7724–7731, 1999).

The following references were cited herein:

1. Darnay and Aggarwal. 1999. Ann. Rheum. Dis. 58 Suppl 1:12.
2. Darnay and Aggarwal. 1997. J Leukoc. Biol. 61:559.
3. Wallach et al. 1999. Ann. Rev. Immunol. 17:331.
4. Hofbauer et al. 2000. J. Bone Miner. Res. 15:2.13
5. Kong et al. 1999. Nature 397:315.
6. Wong et al. 1997. J Exp. Med. 186:2075.
7. Darnay et al. 1998. J Biol. Chem. 273:20551.
8. Darnay et al. 1999. J Biol. Chem. 274:7724.
9. Galibert et al. 1998. J Biol. Chem. 273:34120.
10. Kim et al. 1999. FEBS Lett. 443:297.
11. Hsu et al. 1999. Proc. Natl. Acad. Sci. USA 96:3540.
12. Wong et al. 1998. J Biol. Chem. 273:28355.
13. Pahl. 1999. Oncogene 18:6853.
14. Arch et al. 1998. Genes Dev. 12:2821.
15. McWhirter et al. 1999. Proc. Natl. Acad. Sci. USA 96:8408.
16. Park et al. 1999. Nature 398:533.
17. Pullen et al. 1999. J Biol. Chem,. 274:14246.
18. Wong et al. 1999. Mol. Cell 4:1041.
19. Bucay et al. 1998. Genes Dev. 12:1260.
20. Mizuno et al. 1998. Biochem. Biophys. Res. Commun. 247:610.
21. Li et al. 2000. Proc. Natl. Acad. Sci. USA 97:1566.
22. Dougall et al. 1999. Genes Dev. 13:2412.
23. Lomaga et al. 1999. Genes Dev. 13:1015.
24. Naito et al. 1999. Genes Cells 4:353.
25. Kobayashi et al. 2001. EMBO J 20:1271.
26. Soriano et al. 1991. Cell 64:693.
27. Johnson et al. 1992. Cell 71:577.
28. Iotsova et al. 1997. Nat. Med. 3:1285.
29. Franzoso et al. 1997. Genes Dev. 11:3482.
30. Shevde et al. 2000. Proc. Natl. Acad. Sci. USA 97:7829.
31. Akiba et al. 1998. J Biol. Chem. 273:13353.
32. Hu et al. 1996. Genes Dev. 10:2251.
33. Yao et al. 1999. J Biol. Chem. 274:2118.
34. Haridas et al. 1998. J Immunol. 160:3152.
35. Schwarze et al. 2000. Trends Cell Biol. 10:290.
36. Yan et al. 2000. J Biol. Chem. 275:16774.
37. Wei et al. 2001. Endocrinology 142:1290.
38. Ishida et al. 1996. J Biol. Chem. 271:28745.
39. Futaki et al. 2001. J Biol. Chem. 276:5836.
40. Horwell. 1995. Trends Biotechnol. 13:132.
41. Wexler et al. 1992. Am. J. Hypertens. 5:209S.
42. Saragovi et al. 1992. Biotechnology 10:773.
43. Wesche et al. 1999. J Biol. Chem. 274:19403.

Any patents or publications mentioned in this specification are indicative of the levels of those skilled in the art to which the invention pertains. Further, these patents and publications are incorporated by reference herein to the same extent as if each individual publication is specifically and individually indicated to b e incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A polypeptide that inhibits signaling mediated by TNF receptor-associated factor 6 (TRAF6), wherein said polypeptide comprises a TRAF6 binding domain and a leader signal sequence.

2. The polypeptide of claim 1, wherein said leader signal sequence comprises a polypeptide selected from the group consisting of Kaposi fibroblast growth factor signal sequence, HIV-1 Tat (48–60), D-amino acid-substituted HIV-1 Tat (48–60), arginine-substituted HIV-1 Tat (48–60), Drosophila Antennapaedia (43–58), viral RNA binding peptide that comprises 7 or more arginines, DNA binding peptide that comprises 7 or more arginines and polyarginine polypeptide that has 6 to 8 arginines.

3. The polypeptide of claim 2, wherein said viral RNA binding peptide is selected from the group consisting of HIV-1 Rev (34–50), HTLV-II Rev (4–16), brome mosaic virus Gag (7–25) and flock house virus coat protein (35–49).

4. The polypeptide of claim 2, wherein said DNA binding peptide is selected from the group consisting of human c-Fos (139–164), human c-Jun (252–279) and yeast transcription factor GCN4 (231–252).

5. The polypeptide of claim 1, wherein said TRAF6 binding domain is a TRAF6 binding domain from a protein selected from the group consisting of CD40, Receptor Activator of NF-kB, IL-1 receptor-associated kinase 1 (IRAK1), IL-1 receptor-associated kinase 2 (IRAK2), IRAK-M and RIP2.

6. The polypeptide of claim 5, wherein said TRAF6 binding domain comprises a sequence selected from the group consisting of SEQ ID No. 1–8.

7. The polypeptide of claim 1, wherein said polypeptide comprises a sequence selected from the group consisting of SEQ ID No. 19 and 20.

8. A method of inhibiting receptor activator of NF-kB ligand (RANKL)-induced osteoclast differentiation, comprising the step of:

applying to cells the polypeptide of claim 1, wherein inhibition of interaction between Receptor Activator of NF-kB and TRAF6 by said polypeptide results in inhibition of the receptor activator of NF-kB ligand-induced osteoclast differentiation.

9. The method of claim 8, wherein said polypeptide is delivered to said cells by liposomes.

10. The method of claim 8, wherein said osteoclast differentiation is induced by breast cancer cells.

11. A method of inhibiting osteoclast differentiation in an individual in need of such treatment, comprising the step of:

applying to said individual the polypeptide of claim 1, wherein inhibition of interaction between Receptor Activator of NF-kB and TRAF6 by said polypeptide results in inhibition of osteoclast differentiation.

12. The method of claim 11, wherein said individual has a disease selected from the group consisting of metabolic bone disorders, leukemia, multiple myeloma, arthritis, and metastatic cancer of the bone.

13. A pharmaceutical composition comprising the polypeptide of claim 1 and a pharmaceutically acceptable carrier.

* * * * *

SEQUENCE LISTING

<160> NUMBER OF SEQ ID NOS: 22

<210> SEQ ID NO 1
<211> LENGTH: 9
<212> TYPE: PRT
<213> ORGANISM: Homo sapiens
<220> FEATURE:
<221> NAME/KEY: DOMAIN -continued
<223> OTHER INFORMATION: TRAF6 binding domain from human CD40

<400> SEQUENCE: 1

Lys Gln Glu Pro Gln Glu Ile Asn Phe
            5

<210> SEQ ID NO 2
<211> LENGTH: 9
<212> TYPE: PRT
<213> ORGANISM: Unknown
<220> FEATURE:
<221> NAME/KEY: DOMAIN
<223> OTHER INFORMATION: TRAF6 binding domain from mouse CD40

<400> SEQUENCE: 2

Arg Gln Asp Pro Gln Glu Met Glu Asp
            5

<210> SEQ ID NO 3
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human RANK

<400> SEQUENCE: 3

Arg Gln Met Pro Thr Glu Asp Glu Tyr
            5

<210> SEQ ID NO 4
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human RANK

<400> SEQUENCE: 4

Phe Ser Glu Pro Leu Glu Val Gly Glu
            5

<210> SEQ ID NO 5
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human RANK

<400> SEQUENCE: 5

Arg Asn Pro Pro Gly Glu Asp Cys Glu
            5

<210> SEQ ID NO 6
<211> LENGTH: 9
<212> TYPE: PRT
<213> ORGANISM: Unknown
<220> FEATURE:
<221> NAME/KEY: DOMAIN
<223> OTHER INFORMATION: TRAF6 binding domain from mouse RANK

<400> SEQUENCE: 6

Arg Lys Ile Pro Thr Glu Asp Glu Tyr
            5

<210> SEQ ID NO 7

```
<211> LENGTH: 9
<212> TYPE: PRT
<213> ORGANISM: Unknown
<220> FEATURE:
<221> NAME/KEY: DOMAIN
<223> OTHER INFORMATION: TRAF6 binding domain from mouse RANK

<400> SEQUENCE: 7

Phe Gln Glu Pro Leu Glu Val Gly Glu
                5

<210> SEQ ID NO 8
<211> LENGTH: 9
<212> TYPE: PRT
<213> ORGANISM: Unknown
<220> FEATURE:
<221> NAME/KEY: DOMAIN
<223> OTHER INFORMATION: TRAF6 binding domain from mouse RANK

<400> SEQUENCE: 8

Gly Asn Thr Pro Gly Glu Asp His Glu
                5

<210> SEQ ID NO 9
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human IRAK-1

<400> SEQUENCE: 9

Pro Pro Ser Pro Gln Glu Asn Ser Tyr
                5

<210> SEQ ID NO 10
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human IRAK-1

<400> SEQUENCE: 10

Pro Asn Gln Pro Val Glu Ser Asp Glu
                5

<210> SEQ ID NO 11
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human IRAK-1

<400> SEQUENCE: 11

Arg Gln Gly Pro Glu Glu Ser Asp Glu
                5

<210> SEQ ID NO 12
<211> LENGTH: 9
<212> TYPE: PRT
<213> ORGANISM: Unknown
<220> FEATURE:
<221> NAME/KEY: DOMAIN
<223> OTHER INFORMATION: TRAF6 binding domain from mouse IRAK

<400> SEQUENCE: 12
```

-continued

Ser Pro Ser Pro Gln Glu Asn Ser Tyr
                5

<210> SEQ ID NO 13
<211> LENGTH: 9
<212> TYPE: PRT
<213> ORGANISM: Unknown
<220> FEATURE:
<221> NAME/KEY: DOMAIN
<223> OTHER INFORMATION: TRAF6 binding domain from mouse IRAK

<400> SEQUENCE: 13

Pro Asn Gln Pro Val Glu Ser Asp Glu
                5

<210> SEQ ID NO 14
<211> LENGTH: 9
<212> TYPE: PRT
<213> ORGANISM: Unknown
<220> FEATURE:
<221> NAME/KEY: DOMAIN
<223> OTHER INFORMATION: TRAF6 binding domain from mouse IRAK

<400> SEQUENCE: 14

Ser Gln Gly Pro Glu Glu Ser Asp Glu
                5

<210> SEQ ID NO 15
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human IRAK-2

<400> SEQUENCE: 15

Ser Asn Thr Pro Glu Glu Thr Asp Asp
                5

<210> SEQ ID NO 16
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human IRAK-2

<400> SEQUENCE: 16

Pro Leu Leu Pro Thr Glu Asn Gly Glu
                5

<210> SEQ ID NO 17
<211> LENGTH: 9
<212> TYPE: PRT
<213> ORGANISM: Homo sapiens
<220> FEATURE:
<221> NAME/KEY: DOMAIN
<223> OTHER INFORMATION: TRAF6 binding domain from human IRAK-M

<400> SEQUENCE: 17

Pro Ser Ile Pro Val Glu Asp Asp Glu
                5

<210> SEQ ID NO 18
<211> LENGTH: 9
<212> TYPE: PRT
<213> ORGANISM: Homo sapiens
<220> FEATURE:

```
<221> NAME/KEY: DOMAIN
<223> OTHER INFORMATION: TRAF6 binding domain from human RIP2

<400> SEQUENCE: 18

Ile Tyr Met Pro Pro Glu Asn Tyr Glu
                5

<210> SEQ ID NO 19
<211> LENGTH: 34
<212> TYPE: PRT
<213> ORGANISM: Unknown
<220> FEATURE:
<221> NAME/KEY: PEPTIDE
<223> OTHER INFORMATION: Peptide L-T6Bp-1

<400> SEQUENCE: 19

Ala Ala Val Ala Leu Leu Pro Ala Val Leu Leu Ala Leu Leu Ala
                5                   10                  15

Pro Arg Lys Ile Pro Thr Glu Asp Glu Tyr Thr Asp Arg Pro Ser
                20                  25                  30

Gln Pro Ser Thr

<210> SEQ ID NO 20
<211> LENGTH: 30
<212> TYPE: PRT
<213> ORGANISM: Unknown
<220> FEATURE:
<221> NAME/KEY: PEPTIDE
<223> OTHER INFORMATION: Peptide L-T6Bp-2

<400> SEQUENCE: 20

Ala Ala Val Ala Leu Leu Pro Ala Val Leu Leu Ala Leu Leu Ala
                5                   10                  15

Pro Ile Pro Pro Phe Gln Glu Pro Leu Glu Val Gly Glu Asn Asp
                20                  25                  30

<210> SEQ ID NO 21
<211> LENGTH: 19
<212> TYPE: PRT
<213> ORGANISM: Unknown
<220> FEATURE:
<221> NAME/KEY: PEPTIDE
<223> OTHER INFORMATION: Peptide T6Bp-1

<400> SEQUENCE: 21

Cys Arg Lys Ile Pro Thr Glu Asp Glu Tyr Thr Asp Arg Pro Ser
                5                   10                  15

Gln Pro Ser Thr

<210> SEQ ID NO 22
<211> LENGTH: 15
<212> TYPE: PRT
<213> ORGANISM: Unknown
<220> FEATURE:
<221> NAME/KEY: PEPTIDE
<223> OTHER INFORMATION: Peptide T6Bp-2

<400> SEQUENCE: 22

Cys Ile Pro Pro Phe Gln Glu Pro Leu Glu Val Gly Glu Asn Asp
                5                   10                  15
```